United States Patent
Yasuda et al.

(10) Patent No.: US 8,703,457 B2
(45) Date of Patent: Apr. 22, 2014

(54) CELL SEPARATION APPARATUS

(75) Inventors: Kenji Yasuda, Tokyo (JP); Kazunori Takahashi, Tokyo (JP)

(73) Assignee: On-Chip Cellomics Consortium Co., Ltd., Tokyo (JP)

( * ) Notice: Subject to any disclaimer, the term of this patent is extended or adjusted under 35 U.S.C. 154(b) by 1826 days.

(21) Appl. No.: 10/543,867

(22) PCT Filed: Apr. 30, 2004

(86) PCT No.: PCT/JP2004/006299
§ 371 (c)(1),
(2), (4) Date: Jul. 26, 2005

(87) PCT Pub. No.: WO2004/101731
PCT Pub. Date: Nov. 25, 2004

(65) Prior Publication Data
US 2006/0141618 A1    Jun. 29, 2006

(30) Foreign Application Priority Data

May 19, 2003    (JP) ................................. 2003-139774

(51) Int. Cl.
*C12N 13/00*    (2006.01)
*C12M 1/42*    (2006.01)

(52) U.S. Cl.
USPC .................. 435/173.9; 435/173.1; 435/283.1; 435/307.1; 435/308.1

(58) Field of Classification Search
USPC ........................................... 435/173.1, 173.9
See application file for complete search history.

(56) References Cited

U.S. PATENT DOCUMENTS

| | | | |
|---|---|---|---|
| 4,362,165 A * | 12/1982 | Carmon et al. ............... | 600/396 |
| 5,837,115 A | 11/1998 | Austin et al. | |
| 6,043,066 A * | 3/2000 | Mangano et al. ........... | 435/173.7 |
| 6,245,207 B1 * | 6/2001 | Yasuda et al. ................ | 204/600 |
| 6,403,367 B1 * | 6/2002 | Cheng et al. ............... | 435/287.1 |

FOREIGN PATENT DOCUMENTS

| | | |
|---|---|---|
| EP | 1542007 | 6/2005 |
| GB | 2 071 743 | 9/1981 |
| JP | 2001-178 | 1/2001 |
| JP | 2003-107099 | 4/2003 |
| JP | 2003-265915 | 9/2003 |
| JP | 2003-274924 | 9/2003 |
| JP | 2004-085323 | 3/2004 |
| WO | WO 98/10267 | 3/1998 |
| WO | WO2004/101731 | 11/2004 |

OTHER PUBLICATIONS

Muller, T et al. A 3-D microelectrode system for handling and caging single cells and particles. Biosensors and Bioelectronics. 1999. 14: 247-256.*
English Translation of "Separation and purification of single cells using on-chip cell sorter," Biomaterial. vol. 21, No. 2 pp. 127-132. 2003.*
"Separation and purification of single cells using on-chip cell sorter," Biomaterial. vol. 21, No. 2 pp. 127-132 (2003) [Abstract].
Fiedler et al., "Dielectrophoretic Sorting of Particles and Cells in a Microsystem," Analytical Chemistry. vol. 70, No. 9 pp. 1909-1915 (1998).
International Preliminary Report on Patentability corresponding to International Patent Application No. PCT/JP2004/006299 dated Apr. 28, 2005.
International Search Report corresponding to International Patent Application No. PCT/JP2004/006299 dated Jun. 15, 2004.
Kamarck, M.E., "Flourescence-Activated Cell Sorting of Hybrid and Transfected Cells," Methods in Enzymology. vol. 151 pp. 150-165 (1987).
Wolff et al., "Rare Event Cell Sorting in a Microfluidic System for Application in Prenatal Diagnosis," Proc. of the Micro Total Analysis Systems (μ-TAS1998). vol. 98 pp. 77-80 (1998).
Supplementary European Search Report corresponding to European Patent Application No. 04730647.7-1521 dated Jul. 7, 2009.

* cited by examiner

*Primary Examiner* — Allison Ford
*Assistant Examiner* — Susan E Fernandez
(74) *Attorney, Agent, or Firm* — Jenkins, Wilson, Taylor & Hunt, P.A.

(57) ABSTRACT

A cell separation apparatus comprises a means for moving a cell within a cell separating space by applying an electrical voltage to cells in the cell separating space using gel electrodes, and channels for separating and discharging the cell, which thus does not damage a cell sample and prevents the exhaustion of an electrode due to its electrolysis.

9 Claims, 4 Drawing Sheets a electric field off b electric field on

CELL SEPARATION APPARATUS

FIELD OF THE INVENTION

The present invention relates to a cell separation apparatus (or cell sorter).

BACKGROUND OF THE INVENTION

It is an important technique in biological and medical analyses to separate and recover a specific cell in a culture solution. When a cell can be separated from other cells by a difference in specific gravity of the cell, the cell can be obtained by a velocity sedimentation method. However, when there is substantially no difference among cells in such a case to distinguish an unsensitized cell and a sensitized cell, it is necessary to separate the cells one by one on the basis of information obtained by dyeing them with a fluorescent antibody or information visually obtained by human eyes.

As an example of this technique, there is a cell sorter. Cell sorter is a technique wherein fluorescent dye-treated cells are isolated in one cell unit and dropped into charged droplets, and a high electric field is applied to the charged droplets during the dropping process in any slope plane direction relation to the dropping direction on the basis of the presence or absence of fluorescence on the cells in the droplets and the extent of the amount of light scattering, whereby the dropping direction is controlled so that the cells are fractionized and recovered in a plurality of containers disposed at the bottom (Kamarck, M. E., Methods Enzymol. Vol. 151, pages 150-167(1987)).

However, this technique has many drawbacks that it is expensive and necessitates a large apparatus, a high electric field such as several thousand bolts and a large amount of samples, the cell is possibly damaged in the process of preparing droplets, the sample cannot directly be observed, etc. In these circumstances, a new cell sorter has recently been developed wherein fine particles are separated under direct microscopic observation in a laminar flow passing through fine channels being cut using a micro processing technique (Micro Total Analysis, 98, pp. 77-80 (Kluwer Academic Publishers, 1998); Analytical Chemistry, 70, pp. 1909-1915 (1998)). However, this cell sorter has a drawback that the speed of response to observation means when separating a sample is slow. Therefore, it is necessary to develop a cell sorter which does not cause any damage to a sample and can treat a sample in a faster response.

In order to solve such problems, the present inventors have already filed a patent application (Patent Application No. 2002-245902) as for a cell analysis and separation apparatus in which a sample is fractionized using a micro processing technique on the basis of the fine structure of the sample and the distribution of fluorescence in the sample whereby the cell sample can be conveniently separated and recovered without damaging the cell sample.

PROBLEMS TO BE SOLVED BY THE PRESENT INVENTION

It is an object of the present invention to provide a cell analysis and separation apparatus which does not damage a cell sample, prevents the exhaustion of an electrode to which an electric voltage is applied in order to separate a cell, and does not occur the clogging of channels when separating a cell over a long period of time.

When a metal electrode is used that directly contacts with a sample solution in a conventional cell analysis and separation apparatus (for example, Patent Application No. 2002-245902), the cell sample may be damaged and the electrode possibly exhausts due to its electrolysis especially when an electric voltage is applied to an electrode over a long period of time. Further, when the purification of a cell is continuously performed over a long period of time, it is necessary to prevent the channels from clogging caused by impurities such as tissue fragments, dusts and the like contained in a sample solution. Therefore there has been a demand for a cell separation apparatus without having these drawbacks.

MEANS TO SOLVE THE PROBLEMS

The cell separation apparatus of the present invention comprises a means for moving a cell in a cell separating space by applying an external force to the cell separating space from outside, and channels capable of separating and discharging the cell, whereby this apparatus can prevent the damage of a cell sample and the exhaustion of an electrode due to its electrolysis. Further, the cell separation apparatus of the present invention may have a means for preventing the channels from clogging by capturing impurities at an upstream portion of a channel where a sample fluid for a cell separating space is introduced.

That is, the present invention is a cell separation apparatus comprising a cell separating space, at least one channel for injecting (introducing) a cell-containing fluid into the cell separating space, at least two channels for discharging fluids from the cell separating space, and a means for applying an external force to a cell in the cell separating space from outside, wherein these channels are disposed such that cells are each discharged from the cell separating space into a different channel depending on whether or not an external force is applied to the cell separating space from outside.

According to this cell separation apparatus, since an external force is applied to a cell in a cell separating space from outside, no electrode directly contacts with a cell-containing solution, which prevents the damaging of a cell sample and also prevent the exhaustion of an electrode due to its electrolysis.

Among means for applying such an external force includes electrostatic force, electrophoretic force, magnetic force, ultrasonic radiation, photo-radiation pressure, etc, and an electrostatic force is conveniently used.

When an electrostatic force is to be used, it can be attained by applying an electric field to a cell separating space with the use of an electrode containing electrolyte.

Among electrolytes usable herein are included generic gels such as agarose, amino pectin, collagen, etc.

Electric voltages to be applied may depend on a target cell, but it is preferable to set them by practically passing a cell so that the target cell can be separated. For example, in a case where an agarose gel is used with a distance between electrodes of from 10 to 15 µm, a white blood cell (the extent of 5 µm) can be separated at an electric voltage of around 40 V.

Further, this cell separation apparatus can install a filter, in the channel for injecting a cell-containing fluid, at a downstream of the injection point and at an upstream of the cell separating space.

The present invention is also a cell separation apparatus comprising a cell separating space, at least one channel for injecting a cell-containing fluid into the cell separating space, at least two channels for discharging fluids from the cell separating space, and a means for applying an external force to a cell in the cell separating space from outside, wherein a filter is disposed, in the channel for injecting a cell-containing fluid, at a downstream of the injection point and at an upstream of the cell separating space, and these channels are disposed such that cells are each discharged from the cell separating space into a different channel depending on whether or not an external force is applied to the cell separating space from outside.

Further, this cell separation apparatus may have two channels for injecting a cell-containing fluid into a cell separating space and two channels for discharging fluids from the cell separating space, wherein these channels are disposed such that, when no external force is applied, a fluid flowed from one of the two injection channels into the cell separating space is passed to substantially one of the two discharge channels while a fluid flowed from another injection channel into the cell separating space is passed to substantially the other of the discharge channels, whereby a cell-containing fluid is passed to only one of the injection channels.

Figure 1:
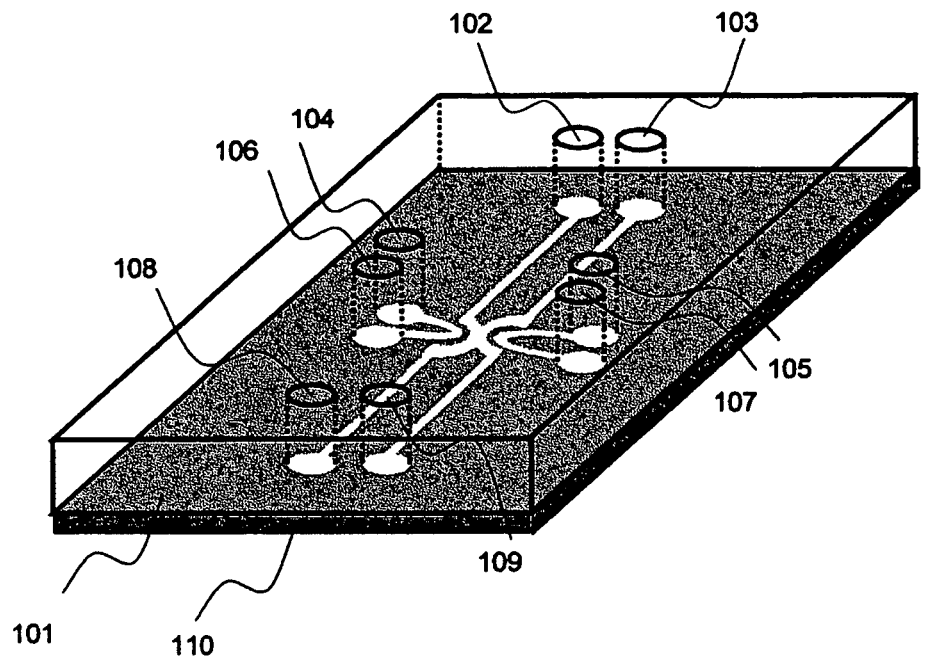
FIG. 1 is a perspective view showing one embodiment of a cell sorter of the present invention.

In these drawings, reference numerals indicate those elements as follows:

101; chip
102, 103, 104, 105, 106, 107, 108, 109; hole
201; injection port for a solution containing a cell
202; injection port for a cell-free solution
206, 207; hole for an electrode
211, 212; cell removal port
203; filter
204, 205, 401, 402, 501, 502; micro-channel
208, 209; electrode (space filled with an electrolyte)
210; cell separating space
301, 304; cell
302, 305; dust
303; column-like structure (filter)
403, 404; gel electrode
405, 406; fine communication opening

EMBODIMENTS OF THE PRESENT INVENTION

Now, one embodiment of a cell separation apparatus of the present invention will be described but the present invention is not to be restricted in any way to this embodiment.

FIG. 1 shows schematically one embodiment of the systematic construction of a cell separation apparatus (cell sorter) of the present invention. This cell sorter is constructed in the form of a channel within a chip 101. The chip has a glass base plate 110 adhesively bonded at its bottom, on which glass base plate is formed a micro-channel. Then, the thickness of the glass base plate is made as thin as possible in order to conduct an optical measurement. For example, when an object lens is used which has a numerical aperture of 1.4 and a factor of 100, it is desirable that the glass base plate has a thickness of 0.2 mm or less. On the top surface of the chip 101, a hole 102 for introducing a sample solution containing a cell into a micro-channel, a hole 103 for introducing a cell-free solution into the micro-channel, holes 104, 105, 106 and 107 for inserting an electrode in a gel electrode, and holes 108 and 109 for recovering the separated and purified cell are formed respectively.

Figure 2:
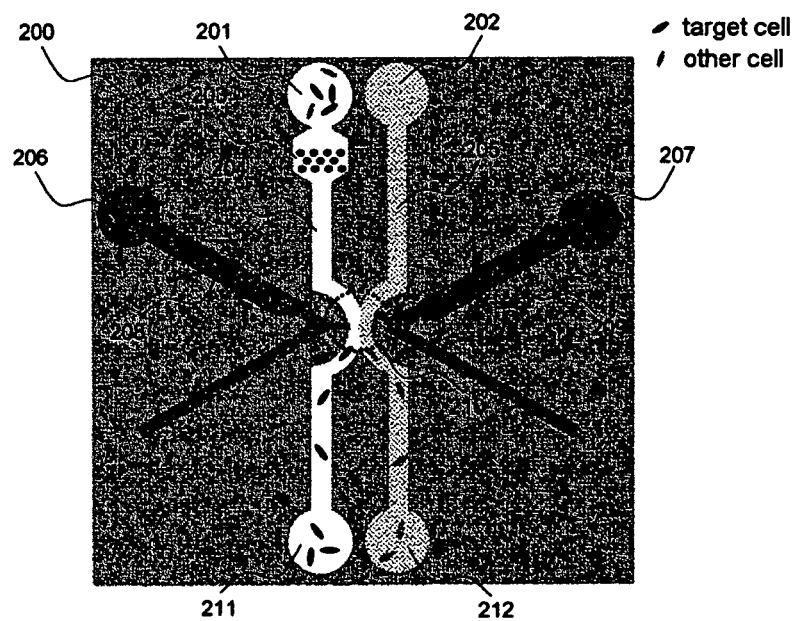
FIG. 2 is a schematic view showing one embodiment of the construction of channels of a cell sorter of the present invention.

FIG. 2 shows schematically one embodiment of the construction of a channel of a cell sorter illustrated in FIG. 1. The cell-containing solution introduced into a hole 201 is passed through a micro-channel 204 up to a cell separating section 210. A filter 203 is disposed at upstream of the micro-channel 204 in order to prevent the clogging of the micro-channel. This filter 203 is directly incorporated in the form of a fine structure into the chip. On the other hand, the cell-free solution introduced into a hole 202 is passed through a channel 205 up to the cell separating section 210 as in the above. The cell separating section 210 is, on its channel 204 side and channel 205 side, respectively, in contact with micro-structures (spaces) 208 and 209 which are filled with a gel containing electrolyte. Thus, an electric field can be applied to the cell separating section 210 through electrodes inserted in holes 206 and 207.

In this cell separating section 210, the stream is in a laminar flow. Thus, when being not subjected to an electric field, a cell flowed from the upstream side of a channel 204 is conveyed to a downstream cell reservoir hole 211. On the other hand, when being subjected to an electric field, the cell is conveyed to a downstream cell reservoir hole 212. Then, the flow rate of the solution can be controlled, for example, by the amount of a solution introduced into holes 201, 202, 211 and 212, that is, a difference in height of the liquid level of the solution. Also, as in this embodiment, when a gel electrode is incorporated into the fine structure of a cell sorter, it is unnecessary to take time for the alignment of a metal electrode with its deposited surface as in a conventional metal electrode.

Figure 3:
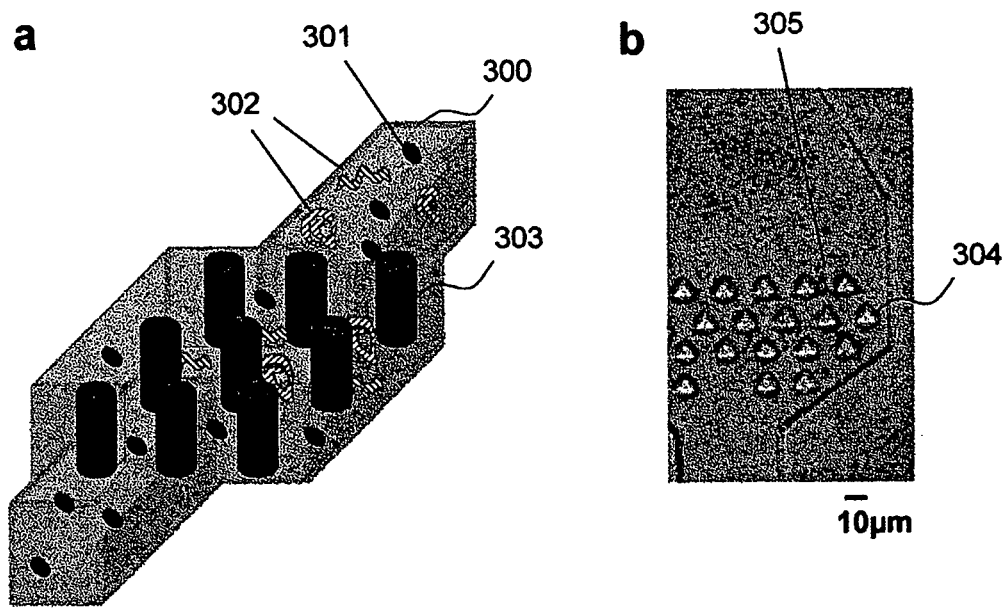
FIG. 3 is a schematic view showing one embodiment of the construction of a filter section of a cell sorter of the present invention.

FIG. 3a is a schematic view showing one embodiment of the structure of a filter section directly incorporated in the form of a fine structure into a chip in order to prevent the clogging of a micro-channel illustrated in FIG. 2. This filter section comprises fine column-like structure 303 periodically disposed and directly embedded in the chip of a cell sorter. Thus, of cells 301 and dusts 302 flowed from the upstream side of the micro-channel, only the dusts 302 are captured by these column-like structures 303 so as to prevent the downstream micro-channel from clogging. FIG. 3b is an optical microphotograph showing one embodiment wherein a filter section is incorporated into the chip of a cell sorter. This microphotograph shows that dusts 305 are captured by column-like structures 304 directly incorporated into the chip. This filter section is of a structure which has an ample width relative to the width of a micro-channel. As a result, even if dusts are captured by these column-like structures, the stream of the channel is not at disturbed all.

Figure 4:
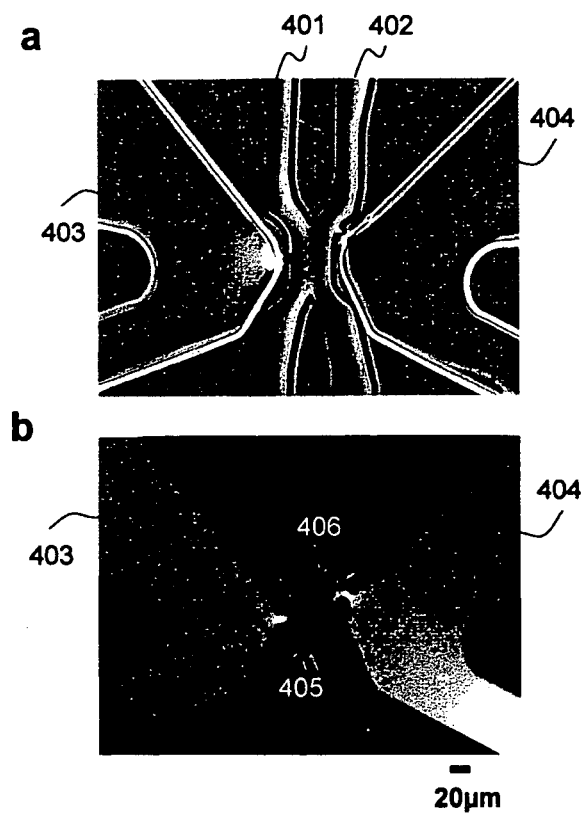
FIG. 4 is a microphotograph showing one embodiment of a cell sorter of the present invention.

FIG. 4 is an optical microscopic image showing the structure of a gel electrode incorporated into a cell sorter. FIG. 4a shows an enlarged observation of the cell separating section of a cell sorter. Gel electrodes 403 and 404 are disposed, respectively, relative to two micro-channels 401 and 402. FIG. 4b shows a fluorescent microscopic observation of gel electrodes having a fluorescent coloring matter incorporated therein. The gel electrodes communicate with channels 401 and 402 through fine communication openings 405 and 406. In this embodiment, a 1% (w/v) agarose is used as the gel electrode, and sodium chloride is used as the electrolyte to be dissolved in the agarose. Further, by maintaining the pH of the cathode side acidic (pH 6.0) and the pH of the anode side basic (pH 8.4), respectively, it is possible to control the generation of a gas in the electrode.

Figure 5:
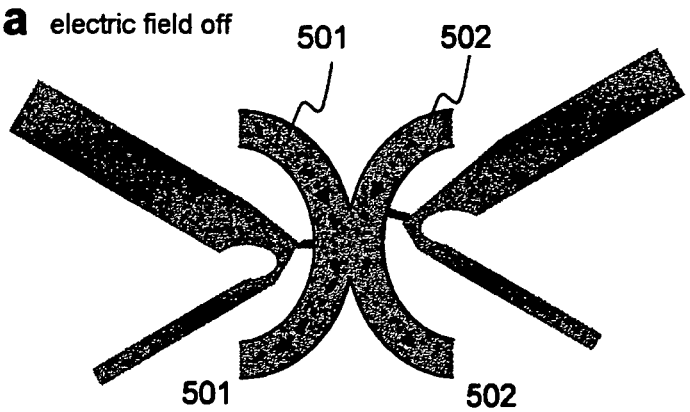
FIG. 5 is a schematic view showing one embodiment of the cell sorting process by a cell sorter of the present invention.
Figure 5:
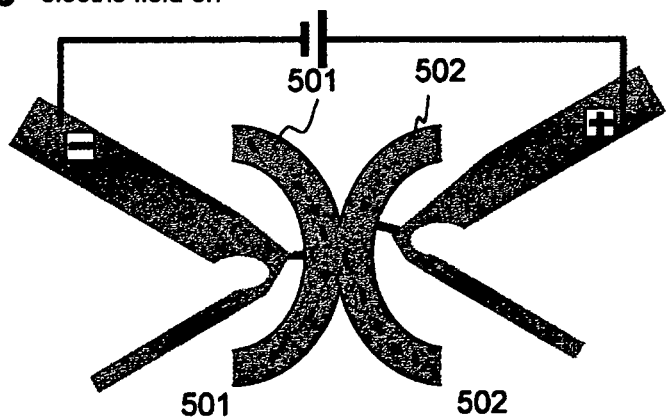

FIG. 5 is a view showing schematically a cell sorting process when actually applying an electric field. When no electric field is applied as in FIG. 5a, the cell run through a channel 501 flows as it is to the downstream direction of the channel 501. On the other hand, when an electric field is applied as in FIG. 5b, the cell run through the channel 501 is transferred to the channel 502.

Figure 6:
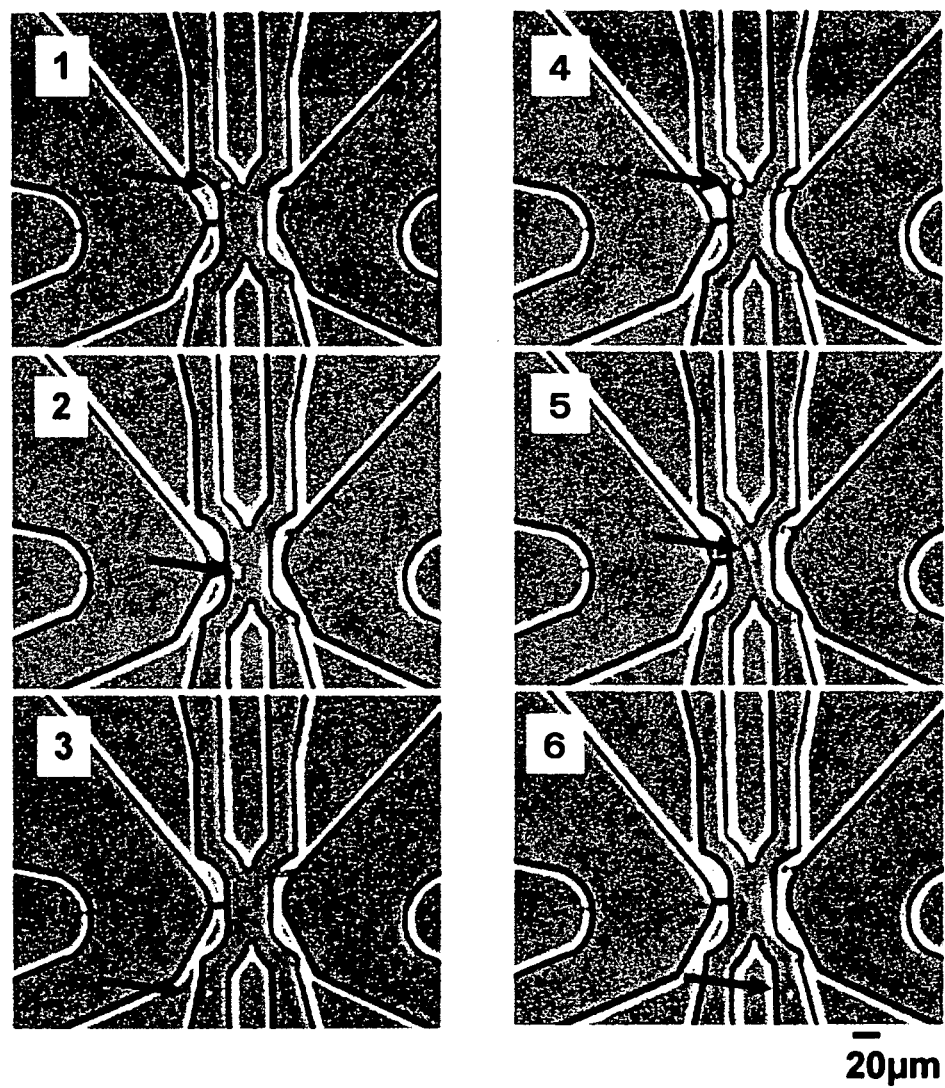
FIG. 6 is a microphotograph showing a cell sorting procedure of the present invention, wherein the arrow indicates a cell.

FIG. 6 is a microphotograph showing a case where a cell is selectively passed to either of two channels in a cell sorter. Referring to continuous photograph Nos. 1-3 of FIG. 6, they show that when no electric field is applied, a cell passes as it is through an identical micro-channel from the upstream side to the downstream side. On the other hand, Nos. 4-6 of FIG. 6 show that when an electric field is applied, a cell moves to another micro-channel.

What is claimed is:

1. A cell separation apparatus comprising a chip and a cell separating space within the chip, at least one channel for injecting a cell-containing fluid into the cell separating space, at least two channels for discharging fluids from the cell separating space, and two gel electrodes each disposed on opposite side walls of the cell separating space, wherein a cell is selectively discharged from the cell separating space into a different channel of the at least two channels depending on whether or not a given electric voltage is applied to the two gel electrodes, wherein the two gel electrodes each contact with the cell-containing fluid through fine communication openings cut on the side walls of the cell separating space, and the communication openings are disposed in relatively deviated position relative to the downstream direction of the fluid.

2. The cell separation apparatus of claim 1, which has two channels for injecting the cell-containing fluid into the cell separating space.

3. The cell separation apparatus of claim 1, wherein a filter is disposed in the at least one channel for injecting a cell-containing fluid, downstream from the injection point and upstream from the cell separating space.

4. A process for the separation of cells with the use of the cell separation apparatus of claim 1, which comprises injecting a cell-containing fluid into the cell separating space, applying selectively a given electric voltage to the two gel electrodes each disposed on opposite side walls of the cell separating space, and discharging selectively a cell contained in the fluid into a different channel of the at least two discharge channels connected to the cell separating space depending on whether or not a given electric voltage is applied to the two gel electrodes.

5. The process for the separation of cells of claim 4, wherein a given electric voltage is applied to the two gel electrodes only when a cell to be recovered flows in the cell separating space.

6. A process for the separation of cells with the use of the cell separation apparatus of claim 2, which comprises injecting a cell-containing fluid into the cell separating space, applying selectively a given electric voltage to the two gel electrodes each disposed on opposite side walls of the cell separating space, and discharging selectively a cell contained in the fluid into a different channel of the at least two discharge channels connected to the cell separating space depending on whether or not a given electric voltage is applied to the two gel electrodes.

7. The process for the separation of cells of claim 6, wherein a given electric voltage is applied to the two gel electrodes only when a cell to be recovered flows in the cell separating space.

8. A cell separation apparatus comprising a chip and a cell separating space within the chip, at least one channel for injecting a cell-containing fluid into the cell separating space, a hole in a top surface of the chip for introducing a cell-containing solution in the at least one channel for injecting a cell-containing fluid, at least one channel for injecting a cell-free fluid into the cell separating space, a hole in the top surface of the chip for introducing a cell-free solution in the at least one channel for injecting a cell-free fluid, at least two channels for discharging fluids from the cell separating space, holes in the top surface of the chip for recovering the separated and purified cell, and two gel electrodes each disposed on opposite side walls of the cell separating space, wherein a cell is selectively discharged from the cell separating space into a different channel of the at least two channels depending on whether or not a given electric voltage is applied to the two gel electrodes, wherein the two gel electrodes each contact with the cell-containing fluid through fine communication openings cut on the side walls of the cell separating space, and the communication openings are disposed in relatively deviated position relative to the downstream direction of the fluid.

9. A process for the separation of cells with the use of the cell separation apparatus of claim 8, which comprises introducing a cell-containing fluid into one of the at least one channel for injecting a cell-containing fluid into the cell separating space, introducing a cell-free fluid into one of the at least one channel for injecting a cell-free fluid into the cell separating space, establishing a laminar flow of the cell-containing fluid in the cell separating space, applying selectively a given electric voltage to the two gel electrodes each disposed on opposite side walls of the cell separating space, and discharging selectively a cell contained in the cell-containing fluid into a different channel of the at least two channels for discharging fluids from the cell separating space connected to the cell separating space depending on whether or not a given electric voltage is applied to the two gel electrodes.

* * * * *